US00PP12377P2

(12) United States Plant Patent
Chang

(10) Patent No.: US PP12,377 P2
(45) Date of Patent: Jan. 29, 2002

(54) STRAWBERRY PLANT CALLED 'GEM STAR'

(76) Inventor: Peggy Pai-Chi Chang, 5983 Green Blvd, Naples, FL (US) 34116

( * ) Notice: Subject to any disclaimer, the term of this patent is extended or adjusted under 35 U.S.C. 154(b) by 0 days.

(21) Appl. No.: 09/497,676

(22) Filed: Feb. 4, 2000

(51) Int. Cl.[7] ..... A01H 5/00
(52) U.S. Cl. ..... Plt./208
(58) Field of Search ..... Plt./208, 209

*Primary Examiner*—Bruce R. Campell
*Assistant Examiner*—Susan B. McCormick

(57) ABSTRACT

'Gem Star' is a new and distinct short-day cultivar of strawberry plant, which produces large ,nice shape ,very glossy and good flavor fruits. Compare to 'Chandler', 'Gem Star' produces more consistent conic to long conic fruit shape, larger primary fruit and the color is lighter red. 'Gem Star' is a vigorous plant, anthracnose crown rot tolerant, early production, high yield, easy to harvest and good flavor. This variety is adapted to growing in the major fruit production areas of the Southeastern United States.

2 Drawing Sheets

BACKGROUND OF THE INVENTION

The invention of 'Gem Star', a new and distinctive cultivar of strawberry plant , is a result of the cross breeding between 'B2' (an unpatented J&P selection) and 'A3' (an unpatented J&P selection). The resulting plant was selected in a controlled breeding plot at J&P Research's cultivated field located in Naples, Fla. during the fruiting season of 1997–1998. It was designated as 'JP2' by the inventor. This cultivar is botanically identified as *Fragaria xananassa Duch.* 'Gem Star' has been propagated by runners and meristem culture in Naples, Fla. as well as in the commercial nurseries in United States and Canada. It has been trialed in the field of growers in North Carolina and Florida. 'Gem Star' plant retains its distinctive characteristics and reproduces true to type in successive generations.

COMPARISON TO CLOSEST CULTIVARS

The commercial cultivar which we believe to be closest to 'Gem Star' from those known to us is 'Chandler', (U.S. Plant Pat. No. 5,262). However, there are several characteristics of 'Gem Star' that are different or not possessed by 'Chandler'. Those are:

(1). Anthracnose crown rot tolerance: The plant of 'Gem Star' is tolerant to anthracnose crown rot disease, which is one of the major diseases in strawberry production in the southeastern United States. 'Chandler' is susceptible to anthracnose disease.

(2). Fruit size: The fruit size of the primary fruit of 'Gem Star' is much larger than that of 'Chandler'.

(3). Fruit color: The fruit color of 'Gem Star' is lighter than that of 'Chandler'.

(4). Isozymes in leaf extracts: isozyme analyses see Table 1. (a) The phosphoglucoisomerase (PGI) isozyme banding pattern for 'Gem Star' is A4 whereas 'Chandler' is A1(b) The leucine aminopeptidase (LAP) isozyme banding pattern for 'Gem Star' and 'Chandler' is B3. (c) The malate dehydrogenase (MDH) isozyme banding for 'Gem Star' is C1 whereas 'Chandler' is C2.

All isozyme analyses were conducted using leaf tissue. Reference: J. Amer. Soc. Hort. Sci. 106:684–687, (1981);

USDA Forest Service General Technical Report PSW-64, (1982); and Tanksley,S. D. and Orton, T. J. Isozymes in Plant Genetics and Breeding, Part A, pp. 469–516 (Elsevier Science Publishers B.V., 1984).

TABLE 1

Isozyme in leaf extracts by electrophoresis

| | 'Gem Star' | 'Chandler' |
|---|---|---|
| PGI | A4 | A1 |
| LAP | B3 | B3 |
| MDH | C1 | C 2 |

As shown in Table 1 'Gem Star' can be unambiguously distinguished from 'Chandler' by using the above-mentioned isozyme patterns.

DESCRIPTION OF THE NEW CULTIVAR

Figure 1:
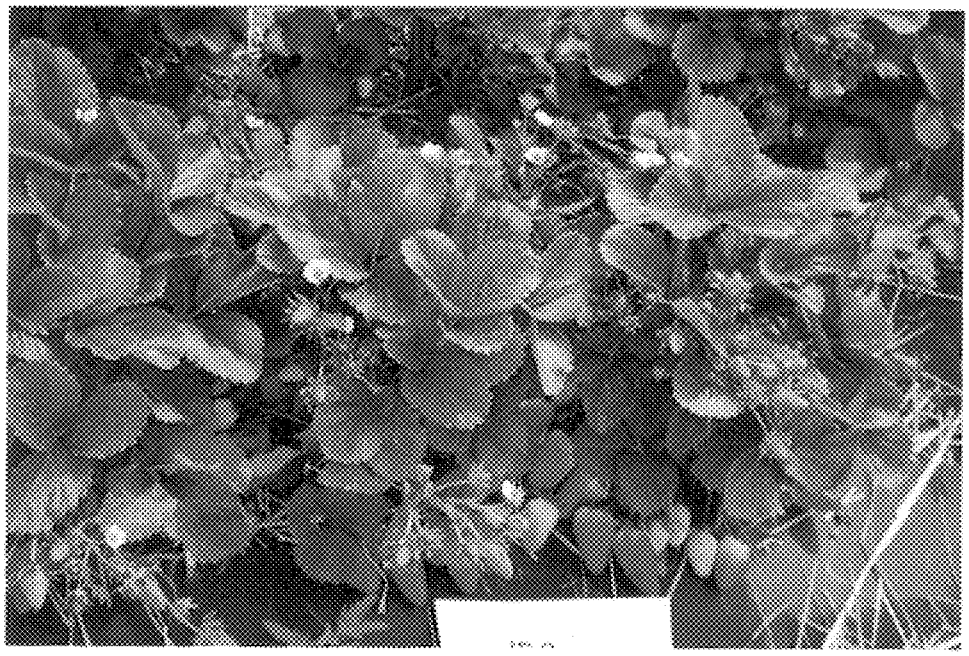
FIG. 1 shows the general flowering and fruiting characteristics of the plants in the production field during the mid-season.
Figure 2:
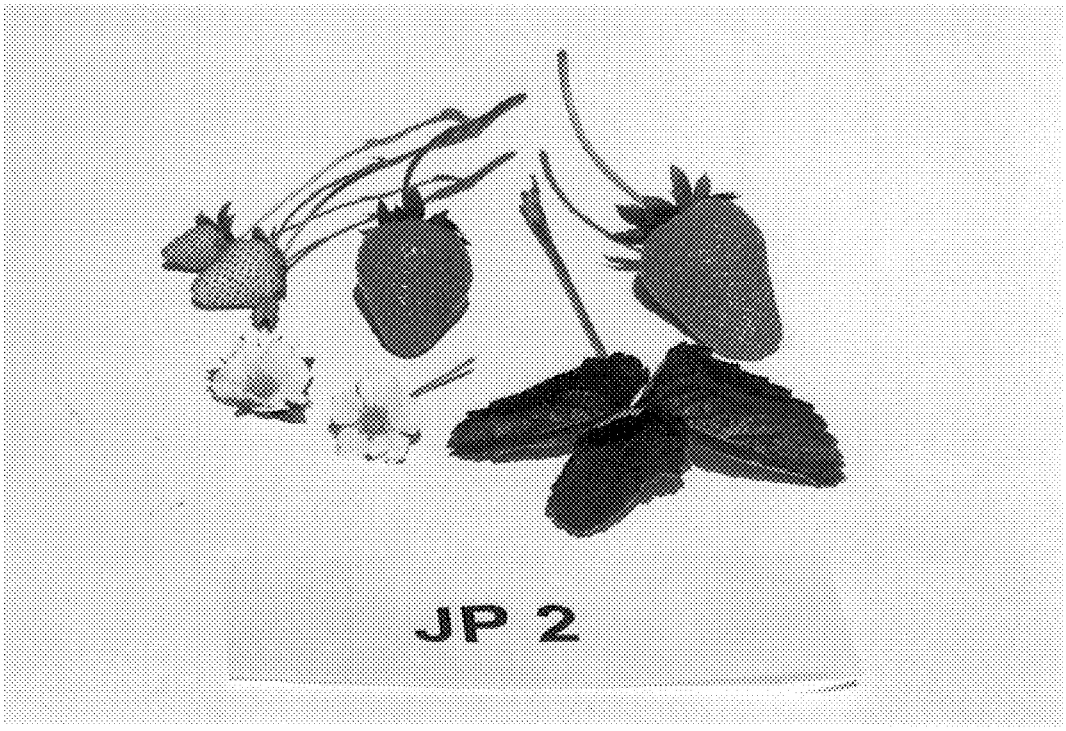
FIG. 2 depicts a) a typical mature compound leaf, b) a representative complete flower in mid-season, c) a fruiting truss including different stages of fruiting and flowering, and d) a typical mature fruit.

'Gem Star' is a new and distinctive short-day type strawberry cultivar which is the result of the cross of 'B2' and 'A3'. The female parent 'B2' possesses the distinguishing characteristics of earliness, high yield, large fruit size, good color, good firm and good flavor. The male parent 'A3', possesses the distinguishing characteristics of very large fruit, good yield, superior shape and glossy color, good flavor and anthracnose tolerance. The novel cultivar 'Gem Star' resembles the female parent in possessing the characteristics of large size and good flavor and resembles the male parent in possessing the characteristics of very large fruit, good flavor and anthracnose tolerance. 'Gem Star' is intermediate between its parents with respect to the characteristics of firmness, fruit shape and color and superior to both parents with respect to yield and earlier production.

'Gem Star' is an early fruiting cultivar with very large and attractive fruits, which has performed well in trials in North Carolina during the 1998–99 fruiting season. It is competitive with 'Chandler' the most important cultivar grown in North Carolina area at this time. 'Gem Star' produces fruits earlier and yields higher than 'Chandler'. 'Gem Star' is a very healthy and vigorous plant, which is tolerant to anthracnose disease and two spotted spider mites.

The distinctive characteristics of this new strawberry cultivar, described in detail below were observed upon its discovery and throughout the repeated test periods.

PLANTS AND FOLIAGE

The plants and foliage characteristics of 'Gem Star' were collected about 4 month after planting the plants in fruiting field are listed in Table 2.

Table 2

Plant & Foliage characteristics for 'Gem Star'

Plant

Average size:
- *Height* (*mm*).—290.
- *Diameter* (*mm*).—325.

Shape: Erect and tall.
Density: Medium to open.
Vigor: Strong.
Root initiation: Fast rooting , about 2 days to 5 days.

Foliage

Terminal leaflet:
- *Length* (*mm*).—66.
- *Width* (*mm*).—62.
- *Shape of terminal leaflet*.—Orbicular with serrulate margin.
- *Color* (*Munsell color charts*).—Abaxial: 5GY 4/4. Adaxial: 5GY 5/4.
- *Leaf pubescence*.—Moderate to sparse and direction is acropetal.
- *Serrations number of terminal leaflets* (*mean*).—22.

Petiole:
- *Length* (*mm*).—216.
- *Diameter* (*mm*).—3.
- *Color* (*Munsell color charts*).—5GY 7/8.
- *Pubescence*.—Heavy and direction is acropetal.

Petiolule:
- *Length* (*mm*).—10.
- *Diameter* (*mm*).—1.5.
- *Color* (*Munsell color charts*).—5GY 6/8.

Base angles of terminal leaflets(half blade) (degree): 66.
Bract leaflet position(distance from base to bract/petiole length): 0.63.
Stolons:
- *Number*.—Many.
- *Anthocyanin coloration*.—Moderate.
- *Thickness* (*diameter, mm*).—2.
- *Pubescence*.—Moderate to sparse and direction is acropetal.

RESISTANCE TO DISEASE , PEST AND STRESS

'Gem Star' is a very healthy and vigorous plant. It is more tolerant to anthracnose crown rot disease than 'Chandler'. 'Gem Star' has a relatively high tolerance to two-spotted spider mites when compared to 'Chandler'. 'Gem Star' is moderately tolerant to high and low temperatures but susceptible to rain cracking. 'Gem Star' is not typically exposed to drought in our growing conditions.

FLOWERING AND FRUITING CHARACTERISTICS

The distinguishing flowering and fruiting characteristics of 'Gem Star' plants were collected about 4–5 month after planting the plants are presented in Table 3. The centers of the fruit are solid showing little to no hollowing. The flowers are self-fertile and pollination is very good.

Table 3

Flower and fruit characters for 'Gem Star'

Bud: In the stage of biggest size, 1 day before flower open.
- *Diameter* (*mm*).—20.
- *Length* (*mm*).—16.
- *Color* (*Munsell color charts*).—Upper: 5GY 7/8. Base: 7.5GY 5/4.

Flower:
- *Diameter* (*mm*).—31.5.
- *Height* (*mm*).—195.
- *Number of flower/cluster*.—About 11.
- *Fragrance*.—None.

Bloom time and period in specific location: Observed at the research plots of J&P Research Inc. in Naples, Fla., on plants planted mid-October.
Approximate of budburst, bloom time & duration: The earliest buds open starting 3 weeks after after the plants were planted. Plants bloom from November until May.
Petals:
- *Length* (*mm*).—13.
- *Width* (*mm*).—13.
- *Shape*.—Obtuse. Apex: Obtuse. Base: Obtuse.
- *Color* (*no color chart given*).—White.
- *Texture*.—Smooth.
- *Margin*.—Entire.
- *Number*.—mean: About 7. Range: 5–9.

Sepals:
- *Length* (*mm*).—12.
- *Width* (*mm*).—5.
- *Shape*.—Oblanceolate. Apex: Acute. Base: Cuneate.
- *Color* (*Munsell color charts*).—Abaxial: 7.5GY4/4. Adaxial: 7.5GY 5/4.
- *Number*.—About 14. Mean Range: 10–18.

Reproductive organs:
- *Stamens*.—Number: 25–40.
- *Length* (*mm*).—2.5–5.
- *Color* (*Munsell color charts*).—5Y 8/10.
- *Pistils*.—Number & location: About 200–700 pistils attached on the surface of the receptacle.
- *Length* (*mm*).—1–1.5.
- *Color* (*Munsell color charts*).—2.5GY 8/12.

Fruit shape: Long conic.
Fruit size & color:
- *Development stage*.—Green fruit: At maximum size about 1–2 days before starting to turn to pink. size:

length (mm): 31. diameter (mm): 21. color (Munsell color charts): Exterior: 2.5GY 8/4. Flesh: White (no color chart given). Pink fruit: About 1–2 days before red. size: length (mm): About 1–2 days after pink. diameter (mm): color (Munsell color charts): Exterior: 7.5R 5/14. Flesh: 7.5R 5/12. Ripe fruit-red size: length (mm): 46. diameter (mm): 41. weight (gram/fruit): Average: 25.7. Primary: 33.3. color (Munsell color charts): Exterior: 7.5R 4/16–7.5R 5/16. Flesh: 7.5R 5/14. Red color from tip to shoulder.

Peduncle:

*Of flowers*.—Length (mm): 21.5. Diameter (mm): 3. Color (Munsell color charts): 5GY 7/8.

Peduncle:

*Of flower*.—Length (mm): 21.5. Diameter (mm): 3. Color(Munsell color charts): 5'GY 6/8.

*of fruits*. —Length (mm): 21.5. Diameter (mm): 3. Color (Munsell color charts): 5'GY 6/8.

*Of fruits*.—Length (mm): 24. Diameter (mm): 4. Color (Munsell color charts): 5GY 6/8.

Pedicel:

Seeds:

*Number* (*mean*).—Primary fruit 666. Secondary fruit: 205.

*Shape*.—Ovate.

*Size*.—length (mm): 1–1.5. diameter (mm): 0.5–1.

*Color* (*Munsell color charts*).—Red 10R 6/10–Yellow 5Y 8/10.

Calyx position: Even/slight indent.

Seed position: Even.

The yield of 'Gem Star' is compared below with that of 'Chandler' in Table 4.

TABLE 4

Data on yield and fruit size of 'Gem Star' vs 'Chandler' obtained from the fruiting season of 1997–98 at J& P Research field in Naples, Florida and 1998–99 at Vernon G. James Research and Extension Center in Plymouth, NC.

| Year | Location | | | Gem Star | Chandler |
|---|---|---|---|---|---|
| 1997–98 | Naples, FL | Yield (gram/plt) | January | 154 | 99 |
| | | | February | 107 | 149 |
| | | | March | 51 | 31 |
| | | | Jan–Mar | 312 | 279 |
| | | Size (gram/fruit) | Average | 26 | 20 |
| | | | Primary | 36 | 30 |

TABLE 4-continued

Data on yield and fruit size of 'Gem Star' vs 'Chandler' obtained from the fruiting season of 1997–98 at J& P Research field in Naples, Florida and 1998–99 at Vernon G. James Research and Extension Center in Plymouth, NC.

| Year | Location | | | Gem Star | Chandler |
|---|---|---|---|---|---|
| 1998–99 | Plymouth, NC | Yield (gram/plant) | Total | 491 | 395 |
| | | Size (gram/fruit) | Average | 107 | 52 |

The Firmness and Sugar Content of 'Gem Star' are present in Table 5.

TABLE 5

| | | |
|---|---|---|
| Firmness (Fruit Pressure Tester) (gram per 5 mm diameter plunger tip) (Higher value firmer fruit) | mean | 447 |
| | range | 290–550 |
| Sugar content (a.k.a.Soluble Solids) (degree Brix) | mean | 10.2 |

Yield of 'Gem Star' is higher than that of 'Chandler'. The fruit size of primary fruit of 'Gem Star' is very large in comparison with that of 'Chandler'. The average fruit size of 'Gem Star' is also larger than that of 'Chandler'. The fruit of 'Gem Star' is moderate firm. The flavor of 'Gem Star' is very good and aromatic. The fruit skin color of 'Gem Star' is lighter than that of 'Chandler'. The finish is very glossy and very attractive. The flesh color and the core are about the same as the skin and only slightly less intense. The calyx is small and positioned even or slight indent with the base of the fruit. Seed placement is positioned even with the skin surface. The fruit is recommended for fresh market.

Because of its earliness, high yield, excellent fruit quality and vigorous healthy plant, this cultivar is considered to competitive in the strawberry industry in Southeast United States.

We claim:

1. A new and distinct cultivar of strawberry plant named 'Gem Star', as herein described and illustrated.

* * * * *